(12) United States Patent
Baum et al.

(10) Patent No.: US 6,458,984 B1
(45) Date of Patent: Oct. 1, 2002

(54) CHEMICAL METHOD FOR REMOVAL AND ANALYSIS OF BORON IMPURITIES IN TETRAETHYLORTHOSILICATE (TEOS)

(75) Inventors: Thomas H. Baum, New Fairfield; Chongying Xu, New Milford, both of CT (US); Frank R. Hedges, Duncanville, TX (US); David Daniel Bernhard, Dallas, TX (US); Brian L. Benac, Austin, TX (US); Scott L. Battle, Cedar Park, TX (US); John M. Lansdown, Austin, TX (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 09/540,584

(22) Filed: Mar. 31, 2000

(51) Int. Cl.$^7$ .................................................. C07F 7/04
(52) U.S. Cl. ......................... 556/466; 436/72; 423/335
(58) Field of Search ........................... 556/466; 436/72; 423/335

(56) References Cited

U.S. PATENT DOCUMENTS

| 5,545,743 A | * | 8/1996 | Cannady et al. ............. 556/466 |
| 5,723,644 A | * | 3/1998 | Tzou ........................... 556/466 |
| 5,902,893 A | | 5/1999 | Laxman |

OTHER PUBLICATIONS

R. K. Laxman, A. K. Hochberg and M. J. Jahl, "Boron Determination in TEOS and Reduction of Boron in SIMOX--SOI Process", 1969.

* cited by examiner

Primary Examiner—Paul F. Shaver
(74) Attorney, Agent, or Firm—Margaret Chappuis; Robert A. McLauchlan

(57) ABSTRACT

A method of purifying tetraethylorthosilicate (TEOS) to remove boron impurities therefrom, and a related method of analyzing TEOS to determine concentration of boron impurities therein.

32 Claims, 1 Drawing Sheet

Figure 1:
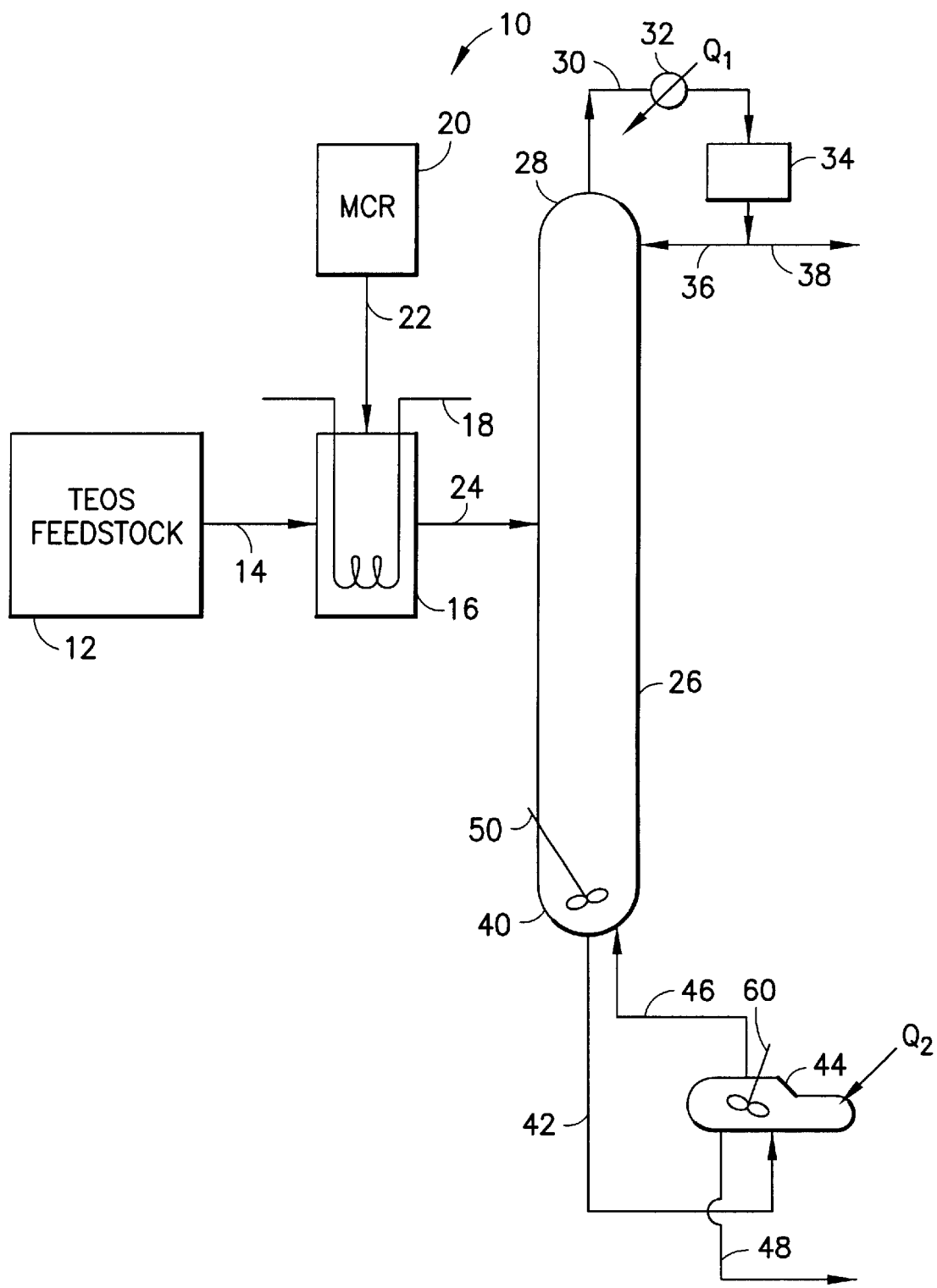

CHEMICAL METHOD FOR REMOVAL AND ANALYSIS OF BORON IMPURITIES IN TETRAETHYLORTHOSILICATE (TEOS)

BACKGROUND OF THE INVENTION

1. Field of the Invention

The present invention relates generally to a method for purifying silanes such as tetraethylorthosilicate (TEOS) to remove boron impurities therefrom, as well to as a method of analysis of analyzing boron impurities in such silanes.

2. Description of the Related Art

In the fabrication of microelectronic devices, current thin-film fabrication techniques require ultra-high purity precursors for depositing specific films. As device densities increase and critical dimensions decrease, electrical requirements of constituent thin-films become increasingly critical.

For example, dielectric films used to insulate gate and multi-level interconnect structures are commonly formed of silicon dioxide ($SiO_2$) and must possess specific electrical properties. To reliably and reproducibly achieve such electrical properties, the precursors used to deposit the corresponding silicon dioxide thin-films must be of ultra-high purity.

Such precursors include tetraethoxysilane or tetraethylorthosilicate (TEOS). A common impurity in TEOS is triethylborate (TEB). Boron can form oxides of differing electrical properties relative to $SiO_2$. Boron is also a dopant species that is extensively used to influence the charge carrier properties of silicon. In ultra-thin gate dielectrics, the diffusion of boron impurities can change the dopant concentration in silicon and thus, alter the performance of a specific transistor junction.

For this reason, the presence of excess boron in the $SiO_2$ layer can be problematic. In fact, it has been shown that boron impurities ranging from 40–80 parts per billion (ppb) can result in boron concentrations in the deposited film of $10^{17}$ atoms/cc as determined by SIMS (see R. K. Laxman, A. K. Hochberg and M. J. Jahl, "Boron Determination in TEOS and Reduction of Boron in SIMOX-SOI Process").

For these reasons, integrated circuitry (IC) manufacturers require boron concentration to be $<10^{15}$ atoms/cc in the $SiO_2$ film for optimized performance.

Since the film growth conversion efficiency for boron-containing molecules in TEOS is relatively high (R. K. Laxman, A. K. Hochberg and M. J. Jahl, "Boron Determination in TEOS and Reduction of Boron in SIMOX-SOI Process"), the concentration of boron impurities typically must be less than 10 ppb in the TEOS starting material to realize good device quality characteristics in the final product.

SUMMARY OF THE INVENTION

The present invention relates to removal and analysis of boron impurities present in silane materials, e.g., TEOS, in connection with the use of such silanes as chemical reagents.

In one aspect, the invention relates to a process for purification of a silane material containing a boron impurity, comprising contacting the silane material with a multifunctional chelating reactant (MCR) for reaction of the boron impurity therewith, to yield an organoborate chelate as a reaction product, and separating the organoborate chelate from the silane material to recover a purified silane material.

Another aspect of the invention relates to a method of determining the amount of boron impurity in a sample of a silane material containing same, comprising the steps of: contacting the silane material with an MCR for reaction of the boron impurity therewith, to yield an organoborate chelate as a reaction product; separating the organoborate chelate from the silane material to recover a purified silane material; and quantitatively assaying the amount of the organoborate chelate to identify the amount of boron impurity in the sample.

As used herein, the term "multifunctional chelating reactant" or "MCR" refers to a chemical agent that is (1) reactive with boron species having the formula B(RR'R"), wherein each of R is same or different and selected from the group consisting of hydroxyl, $C_1$–$C_8$ alkoxy and $C_1$–$C_8$ alkyl, and (2) reactive with such R, R' and R" groups to form protonated reaction by-products.

In one aspect of the invention the MCR is reactive with TEB to form a donor acceptor complex and alcohol as a reaction by-product.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Although described hereinafter primarily in reference to TEOS, it will be appreciated that the method of the invention is not thus limited, but rather is broadly applicable to the purification and analysis of other alkoxysilanes, as well as alkylsilanes, and mixtures of the foregoing. The ensuing discussion relating to TEOS should therefore be understood to encompass such other silane materials, as variant feedstocks to which the purification/analysis methodology of the invention is usefully applied.

The present invention provides a method for obtaining high levels of TEOS purity, suitable for semiconductor device manufacturing applications, in which the TEOS is useful to form $SiO_2$ films of corresponding high purity.

The present invention also provides in one aspect a method of analyzing TEOS to determine the level of purity thereof, for applications such as integrated circuitry manufacturing requiring >99.999% and more preferably >99.99999 elemental purity of the TEOS reagent.

The present invention allows boron species having the formula B(RR'R"), wherein each of R is same or different and selected from the group consisting of hydroxyl, $C_1$–$C_8$ alkoxy and $C_1$–$C_8$ alkyl, to be chelated and removed from the TEOS. Common boron impurities such as triethylborate (TEB) may be greatly reduced in the purified TEOS product, e.g., to levels <10ppb boron.

The boron impurity that invariably is present in TEOS produced for microelectronics fabrication applications is triethylborate (TEB). The method of the present invention enables TEB to be reduced to levels <0.001% and more preferably to <0.00001 % in the purified TEOS product.

The purification and analysis reagent compositions useful in the practice of the invention may alternatively comprise, consist of, or consist essentially of any of the purification/analysis components hereinafter described, and such compositions may additionally, or alternatively, exclude or be substantially free of any components not specifically described herein as being included or includable in such compositions.

The purification/analysis compositions of the invention in one aspect comprise one or more multifunctional chelating reactants (MCRs) that react with boron to form an organoborate chelate, preferably a nitrogen-containing organoborate chelate, having a boiling point above that of TEOS, preferably at least 50° C. above that of TEOS, more preferably at least 80° C. and most preferably at least 100° C. above such boiling point of TEOS.

The MCRs of the invention that are employed to form a nitrogen-containing organoborate chelate as the reaction product of the MCR and the boron impurity, can be of any suitable type. Such MCRs correspondingly include nitrogen, preferably as an amine functionality of the MCR, or alternatively in the form of imine or nitrile functionality. In the chelated reaction product of the MCR and the boron impurity, the electron-rich nitrogen constituent deriving from the MCR coordinates to the electron-deficient boron central atom to form a highly stable chelate as the coordination complex reaction product. A preferred class of such MCRs includes multifunctional organoamines, such as alkylamines and aminoalkylamines. A highly preferred MCR of such type is tris(2-aminoethyl)amine.

The MCRs of the invention in one embodiment include oxygen-containing functionality that reacts with the boron impurities in the TEOS to form the organoborate chelate reaction product. The oxygen functionality of the MCR is preferably a hydroxyl functionality, or alternatively carboxyl or carboxamide functionality. A preferred class of such MCRs includes multifunctional organooxy compounds, such as multifunctional alcohols, glycols and other polyols.

A particularly preferred class of MCRs in the practice of the invention includes multifunctional chelating species, e.g., organooxyamines, organohydroxyamines such as triethanolamine, trimethanolamine, and the like.

A highly preferred MCR is triethanolamine (TEA), which is reactive with TEB to form a donor acceptor complex including ethoxy groups, and reactive with the ethoxy groups of the borate to form ethanol as a reaction by-product. TEA serves as a boron getter even at low concentrations in TEOS, because the TEA nitrogen electron lone pair donates electron density to the boron vacancy to form a donor acceptor complex. The general structure of the TEB molecule is shown below in Formula 1:

(Formula 1)

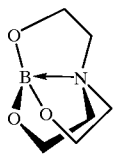

The TEA/TEB reaction is characterized by low energy and is kinetically rapid. Once the donor acceptor complex is formed, the three alcohol groups of the TEA react with the three-borate ethoxy groups to eliminate ethanol. The resulting (end product of the reaction) TEA borate is very stable and non-volatile in character.

TEA is a particularly preferred aminopolyalcohol MCR. TEA is however substantially insoluble in TEOS and therefore the TEA/TEB reaction is advantageously facilitated by vigorous stirring or boiling action in the reaction medium to ensure good contact of the reactants with one another. In some applications, it may be desirable to enhance the solubility of TEA in TEOS by use of TEA analogs, e.g., triolamines having alkane substituents such as butyl groups, pendant on the C1 carbons of the TEA molecular structure.

The MCR compositions of the invention are utilized in the purification/analysis method of the invention to react with the boron impurities of the raw or feedstock TEOS to yield an organoborate chelate which is readily removable from the bulk TEOS by simple distillation to produce TEOS that is purified of such boron impurity.

In the purification aspect of the invention, the resulting distilled TEOS is a high purity product suitable for microelectronic device manufacture, as a source reagent for silicon dioxide.

In the analysis aspect of the invention, the wide separation of the boiling points of the chelate and the TEOS or other silane material, permits the chelate to be quantitatively recovered and assayed to determine the amount of the boron impurity in the TEOS or other silane material with a high precision. After quantitatively removing and recovering boron, conventional analytical methods such as ICP/MS may be used for further analysis of the recovered material. The invention thereby enables ultra-high purity (ppb) analyses of TEOS, related alkoxysilanes, alkylsilanes and mixtures thereof, for semiconductor applications.

By virtue of its high boiling point in relation to TEOS, the organoborate chelate is readily removed by distillation from the TEOS with which the MCR has been contacted, to yield a high purity (99.999999%+ and preferably 99.9999999%+ purity, on a weight basis) TEOS product.

The MCRs employed in the invention have boiling points that are sufficiently different from the boiling points of either TEOS (boiling point=168.9° C.) or the organoborate chelates produced by the MCR reaction, so that unreacted MCR does not itself interfere with the distillative process in the purification/analysis method of the invention.

In a preferred embodiment of the method of the invention for purification of TEOS, the MCR composition is added to the TEOS feedstock (boron impurity-containing TEOS) prior to or during distillation. The reaction between the MCR and the boron impurity is thereby carried out at ambient temperature, or at elevated temperature, as necessary or desired in a given application of the invention. Elevated temperature conditions will favor the reaction kinetics of the organoborate formation reaction, and the purification process system for such purpose can advantageously include a reaction chamber upstream of the distillation apparatus in which the MCR composition is added to the boron impurity-containing TEOS. The reaction chamber in such arrangement can be heated to facilitate the reaction forming the organoborate chelate, and the reaction chamber is suitably sized to provide the appropriate contact/residence time for the reaction.

An illustrative process system for purification of boron impurity-containing TEOS is schematically depicted in FIG. 1.

As illustrated, the process system 10 includes a vessel 12 containing TEOS including boron impurity species therein ("TEOS FEEDSTOCK"), from which the boron impurity-containing TEOS liquid is flowed in line 14 to chemical purification reactor 16. The reactor 16 is equipped with heating means 18.

The heating means can be of any suitable type, with the illustrated element being a heat exchange passage through which a heating medium can be flowed, to heat the TEOS feedstock in the vessel. Alternatively, the heating means can include a heating jacket, a resistance heating coil positioned in the interior liquid-holding volume of the vessel 16, a steam-tracing conduit or jacket on line 14, infrared heating lamps, etc.

The heating means 18 is an optional feature since as mentioned the reaction of the MCR and the TEOS feedstock may be carried out at ambient temperature, but heating of the reaction medium affords the advantage of faster reaction rates and smaller vessel size, as compared to ambient temperature reaction.

The MCR is provided from a source vessel 20 and may be flowed to the reaction vessel 16 via line 22, or alternatively dosed into the liquid reaction volume via an automatic dose metering system (not shown in FIG. 1).

The reaction of the MCR with the boron impurities in the TEOS feedstock produces a chelated organoborane reaction product in the reaction vessel 16. For example, the TEOS feedstock may illustratively contain 550 parts per billion of triethylborate (TEB) or other boron impurity containing from about 2 to about 10 percent elemental boron, based on the molecular weight thereof. The TEB impurity reacts with triethanolamine (TEA) as the MCR, to form triethylamine borate (TEAB) as the organoborate reaction product. Some ethanol is formed as a side-product of the reaction, but ethanol is low boiling (bp=78° C.) and easily separated from the distilling TEOS. The MCR co-reactant desirably is added in stoichiometric excess to ensure maximal reaction of the boron impurity species in the TEOS feedstock. The reaction volume in this illustrative embodiment will then include TEOS, TEA, TEB and TEAB, as well as by-product alcohol.

The volumetric flow rate of TEOS feedstock to the vessel 16 can be controlled by flow control means, e.g., mass flow controllers, automatic flow control valves, etc., to provide a desired residence time of the TEOS feedstock in the vessel for substantially complete reaction.

After the reaction has taken place, the reaction product liquid mixture is flowed in line 24 to the distillation column 26. The distillation column 26 is of conventional construction and has at its overhead portion 28 a total overhead condenser assembly comprising condenser 32 and condensate tank 34 through which overhead flows in line 30.

The overhead vapor is flowed in line 30 to the condenser in which cooling water or other heat exchange medium is flowed to extract heat (enthalpy $Q_1$) of vaporization and effect condensation of the vapor. The vapor then flows into condensate tank 34 from which a portion is recycled as reflux in line 36 to the overhead portion of the column, and a portion is flowed in line 38 out of the system, as high purity TEOS having greatly reduced levels of elemental boron, (e.g., having <10 parts per billion elemental boron impurity).

At the bottom portion 40 of the column 26, bottoms liquid is withdrawn in line 42 and flowed to the reboiler 44 in which the bottoms liquid is partially revaporized by heat input $Q_2$. Resultant reboil vapor is flowed in line 46 back into the lower portion 40 of the column. The bottom product liquid is withdrawn from the reboiler 44 in line 48 and flows to waste or is recycled for further distillation.

The lower portion 40 of the column 26 optionally may have disposed therein an agitator or mixer element 50 to ensure TEA/TEB contact, particularly if the TEA reagent is introduced directly into the column or into feed line 24 as hereafter described. For the same reason, reboiler 44 optionally may have a corresponding agitator or mixer element 60 therein, to effect a suitable level of TEA/TEB contact in view of the negligible solubility of TEA in TEOS.

The bottom product liquid in line 48 is a mixture of the stoichiometric excess reactant TEA, and the reaction product TEAB. The boiling points of the respective components of the liquid flowed to the first column 26 are as follows: TEOS=168.9° C.; TEA=335° C.; and TEAB>350° C. The substantial variance between the TEOS, the MCR and the organoborane chelate facilitates sharp and quantitative separations, and enables the production of ultra-high TEOS.

As an alternative to the use of the reaction vessel 16 in the FIG. 1 system, such system can alternatively be operated with injection of the MCR into line 24 for mixing and reaction with the TEOS feedstock fed to the distillation column 26, thereby obviating the need for any reaction vessel being employed upstream of the column. As another alternative, the MCR may be injected or otherwise introduced directly into the column 26, so that the column serves as a reaction vessel as well as a separation vessel.

Further, although the FIG. 1 embodiment is shown and described as a continuous flow system, it will be appreciated that the system may be constructed and arranged for batch or semi-batch operation, within the broad scope of the present invention.

Although the invention has been variously disclosed herein with reference to illustrative aspects, embodiments and features, it will be appreciated that the aspects, embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. A process for purification of a silane material containing a boron impurity, comprising contacting the silane material with an MCR for reaction of the boron impurity therewith, to yield an organoborate chelate as a reaction product, and separating the organoborate chelate from the silane material to recover a purified silane material.

2. The process of claim 1, wherein the silane material comprises at least one silane species selected from the group consisting of alkoxysilanes, alkylsilanes, and mixtures thereof.

3. The process of claim 1, wherein the silane material comprises TEOS.

4. A $SiO_2$ film made from a silane material purified by the process of claim 1.

5. A method of determining the amount of boron impurity in a sample of a silane material containing same, comprising the steps of: contacting the silane material with an MCR for reaction of the boron impurity therewith, to yield an organoborate chelate as a reaction product; separating the organoborate chelate from the silane material to recover a purified silane material; and quantitatively assaying the amount of the organoborate chelate to identify the amount of boron impurity in the sample.

6. The process of claim 1, wherein the purified silane material comprises TEOS having a purity of >99.999% by weight.

7. The process of claim 1, wherein the boron impurity comprises elemental boron.

8. The process of claim 1, wherein the boron impurity comprises triethylborate (TEB).

9. The process of claim 8, wherein the purified silane material contains <0.00001% TEB.

10. The process of claim 1, Wherein the organoborate chelate comprises a nitrogen-containing organoborate chelate.

11. The process of claim 1, wherein the organoborate chelate has a boiling point above that of TEOS.

12. The process of claim 1, wherein the organoborate chelate has a boiling point at least 50° C. above that of TEOS.

13. The process of claim 1, wherein the organoborate chelate has a boiling point at least 80° C. above that of TEOS.

14. The process of claim 1, wherein the organoborate chelate has a boiling point at least 100° C. above that of TEOS.

15. The process of claim 1, wherein the MRC comprises amine and hydroxy functionality.

16. The process of claim 1, wherein the organoborate chelate comprises a nitrogen-containing organoborate chelate.

17. The process of claim 1, wherein the MCR comprises amine, imine or nitrile functionality.

18. The process of claim 1, wherein the MCR comprises hydroxy, carboxy, or carboxamide functionality.

19. The process of claim 1, wherein the MCR comprises hydroxy functionality.

20. The process of claim 1, wherein the MCR comprises amine functionality.

21. The process of claim 1, wherein the MCR comprises amine organoamine functionality.

22. The process of claim 1, wherein the MCR comprises functionality selected from the group consisting of alkylamines and aminoalkylamines.

23. The process of claim 1, wherein the MCR comprises tris(2-aminoethyl)amine.

24. The process of claim 1, wherein the MCR comprises an organooxy moiety.

25. The process of claim 1, wherein the MCR is selected from the group consisting of multifunctional alcohols, glycols and polyols.

26. The process of claim 1, wherein the MCR is selected from the group consisting of organooxyamines.

27. The process of claim 1, wherein the MCR is selected from the group consisting of triethanolamine, trimethanolamine, and mixtures thereof.

28. The process of claim 27, wherein the silane material comprises a silane species selected from the group consisting of alkoxysilanes, alkylsilanes and mixtures thereof.

29. The process of claim 27, wherein the silane material comprises TEOS.

30. The process of claim 1, wherein the silane material has a purity of 99.99999%+, on a weight basis.

31. The process of claim 1, wherein the silane material has a purity of 99.9999999%+, on a weight basis.

32. The process of claim 1, *herein the MCR comprises TEA.

* * * * *

UNITED STATES PATENT AND TRADEMARK OFFICE
CERTIFICATE OF CORRECTION

PATENT NO. : 6,458,984 B1
DATED : October 1, 2002
INVENTOR(S) : Thomas H. Baum et al.

It is certified that error appears in the above-identified patent and that said Letters Patent is hereby corrected as shown below:

<u>Column 6,</u>
Line 57, cancel "Wherein" and substitute -- wherein --

<u>Column 7,</u>
Line 18, cancel "amine".

<u>Column 8,</u>
Line 20, cancel "*herein" and substitute -- wherein --.

Signed and Sealed this

Fourth Day of November, 2003

JAMES E. ROGAN
*Director of the United States Patent and Trademark Office*